United States Patent [19]

Peterson et al.

[11] 4,237,726

[45] Dec. 9, 1980

[54] PROCESS FOR PREDICTING THE USEFUL LIFE OF A RESPIRATOR CARTRIDGE

[75] Inventors: Robert L. Peterson, Midland, Mich.; Gerald P. Beaumont, Buffalo, W. Va.; Bruce P. Johnson, Tustin, Mich.

[73] Assignee: The Dow Chemical Company, Midland, Mich.

[21] Appl. No.: 62,656

[22] Filed: Aug. 1, 1979

[51] Int. Cl.[3] .............................................. G01N 5/02
[52] U.S. Cl. ........................................ 73/73; 55/270
[58] Field of Search ...................... 73/73; 55/270, 274, 55/275

[56] References Cited

PUBLICATIONS

Ruch, W. E., G. O. Nelson, C. L. Lindeken, R. G. Johnsen and D. J. Hodgkins: Respirator Cartridge Efficiency Studies I. Experimental Design, Am. Ind. Hyg. Association J. 33:105–109 (1972) describes a system designed to determine the service life of respirator cartridges in atmospheres containing organic vapors.

Nelson, G. O. and D. J. Hodgkins: Respirator Cartridge Efficiency Studies II. Preparation of Test Atmospheres, Am. Ind. Hyg. Assoc. J. 33:110–116 (1972) indicates how various test atmospheres can Be prepared which have known concentrations of solvent vapor in humidified air.

Nelson, G. O., R. E. Johnsen, C. L. Lindeken and R. D. Taylor: Respirator Cartridge Efficiency Studies III. A Mechanical Breathing Machine to Simulate Human Respiration, Am. Ind. Hyg. Assoc. J. 33:745–750 (1972), describes a mechanical breathing simulator which can be utilized in a system to determine the service life of respirator cartridges.

Nelson, G. O. and C. A. Harder: Respirator Cartridge Efficiency Studies IV. Effects of Steady-State and Pulsating Flow, Am. Ind. Hyg. Assoc. J. 33:797–805 (1972), evaluates the effects of steady-state and pulsating flows with regard to the service life of respirator cartridges.

Nelson, G. O., and C. A. Harder: Respirator Cartridge Efficiency Studies: V. Effect of Solvent Vapor, Am. Ind. Hyg. Assoc. J. 35:391–410 (1974), describes the effective service life of respirator cartridges when tested with a number of different solvent vapors and gases.

Nelson, G. O. and C. A. Harder: Respirator Cartridge Efficiency Studies: VI. Effect of Concentration, Am. Ind. Hyg. Assoc. J. 37:205–216 (1976), evaluates the effect of various vapor concentrations on the service life of respirator cartridges.

Nelson, G. O., A. N. Correia and C. A. Harder: Respirator Cartridge Efficiency Studies: VII. Effect of Relative Humidity and Temperature, Am. Ind. Hyg. Assoc. J. 37:280–288 (1976), is concerned with the effects of relative humidity and temperature on the service life of respirator cartridges.

Nelson, G. O. and A. N. Correia: Respirator Cartridge Efficiency Studies: VIII. Summary and Conclusions, Am. Ind. Hyg. Assoc. J. 37:514–525 (1976), describes the summary and conclusions of previous work as well as presenting various theoretical interpretations of solvent vapor adsorption on activated carbon.

Nelson, G. O., L. E. Swisher, R. D. Taylor and B. E. Bigler: Preparation of Mixtures of Humidified Air with CO, $SO_2$, $NO_2$, $NH_3$, $NH_2CH_3$, $Cl_2$, and HCl to Measure Respirator Cartridge and Canister Service Life, Am. Ind. Hyg. Assoc. J. 36:49–56 (1975), describes the preparation of various humidified air and contaminant gas mixtures.

NIOSH Research Report, Development of Improved Respirator Cartridge and Canister Test Methods, HEW Jul. 1977 reviews some of the literature and findings pertaining to the prediction of service life and adsorption capacity of respirator cartridges and canisters.

*Primary Examiner*—Donald O. Woodiel

[57] ABSTRACT

A process for predicting the useful life of a respirator cartridge when used in an environment in which a specified toxic or hazardous organic vapor is present by measuring the weight increase of a preselected sorptive agent in a preselected geometrical configuration when exposed to a constant flow rate of a mixture of known concentration, said mixture consisting of dry air having the toxic or hazardous organic vapor dispersed therein. The invention also includes a kit consisting of some or all of the apparatus or equipment essential for practicing the present invention.

5 Claims, 1 Drawing Figure

PROCESS FOR PREDICTING THE USEFUL LIFE OF A RESPIRATOR CARTRIDGE

BACKGROUND OF THE INVENTION

Organic vapor respirators, hereafter called respirators, are used as a means of protecting individuals from the inhalation of organic vapors. The protection provided by the respirator is derived from the use of an adsorbent, generally activated carbon, which adsorbs the organic vapor. Normally, the adsorbent is held in a cartridge or canister which can be replaced when the adsorbent loses its effectiveness, i.e., when the individual is no longer protected by the respirator because the adsorbent has lost its ability to remove toxic amounts of the organic vapor from the air. However, the duration of effective protection varies and depends upon a number of parameters such as the quantity of adsorbent, the particular organic vapor, the concentration of the organic vapor in the air, the humidity, the temperature, the nature and condition of the adsorbent, etc.

Because of this variability in the length of cartridge effectiveness, a number of attempts have been made to assess these parameters and derive a means of predicting the duration of cartridge protection in particular environments.

Current methods of determining respirator cartridge life are complicated, slow and expensive; therefore many organic vapors are completely untested, or untested in a variety of environments. Conventional respirator testing is performed with an apparatus similar to that described by Walter E. Ruch et al.: Respirator Cartridge Efficiency Studies I. Experimental Design, Am. Ind. Hyg. Assoc. J. 33: 105, 107 (1972) and Gary O. Nelson et al.: Respirator Cartridge Efficiency Studies II. Preparation of Test Atmospheres, Am. Ind. Hyg. Assoc. J. 33: 110, 111, 112 (1972).

In the conventional method a dynamic apparatus, an apparatus which continually produces a known concentration of a humidity-adjusted air/organic vapor mix, generates a flow of contaminant organic vapor mixed with air. The air/organic vapor mix is passed through an upstream analyzer, i.e., an analyzer positioned to measure the contaminant concentration before it reaches the respirator cartridge, and a second analyzer downstream which measures the contaminant level after the air/organic vapor mix has passed through the respirator cartridge being tested. The respirator cartridge life, also known as the breakthrough time, is that time duration measured from the time of the initial exposure of the respirator cartridge to the organic vapor contaminant to the time at which the contaminant is no longer completely retained by the cartridge. When the organic vapor traverses the respirator cartridge it is detected by the downstream analyzer.

SUMMARY OF THE INVENTION

The present invention is directed to a process for predicting the useful respirator cartridge lifetime for a preselected sorptive agent employed at a predetermined bed depth when exposed to a specified toxic or hazardous organic vapor, in which process a dry air/organic vapor mixture of known composition is drawn through a pre-weighed test charge of the sorptive agent disposed in a cylinder to the predetermined depth, and the cylinder periodically and repeatedly disconnected from the system after about 1 to about 3 minute periods of exposure to the dry air/organic vapor mixture, and the cylinder and contents reweighed until it is determined that the rate of weight increase with increased exposure has fallen off, indicating breakthrough for the test charge, and making a simple calculation to determine the useful life for the entire respirator cartridge.

The invention also contemplates a kit consisting of some or all of the apparatus and equipment items essential for practicing the present invention.

The FIGURE of the drawing shows a graph depicting breakthrough time determination for a test sample.

DETAILED DESCRIPTION OF THE INVENTION

Figure 1:
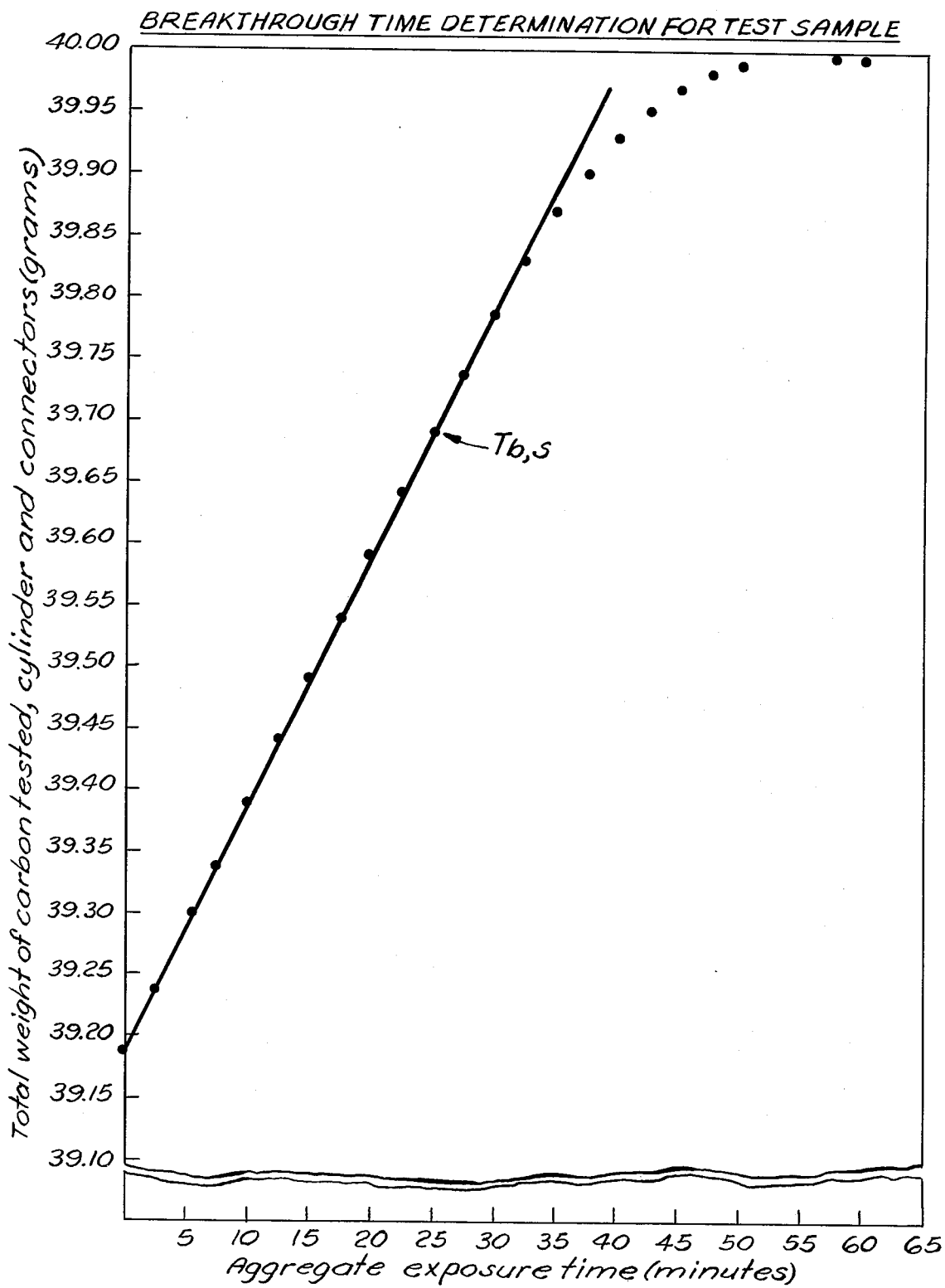

In the present invention a predetermined quantity of sorptive agent is exposed to a constant flow rate of a dry air/organic vapor mixture of known concentration. The invention can be used to evaluate any adsorptive material proposed for use as a sorptive agent in a respirator cartridge which is capable of the physical adsorption of a toxic or hazardous organic vapor without the production of chemical by-products; such that the proposed sorptive agent removes organic vapor from dry air at a constant rate at least until breakthrough occurs. Among the sorptive agents that are available, activated carbon, hereafter referred to as carbon, is the sorptive agent most generally utilized in respirators. Respirator cartridge lifetime is determined by monitoring the rate at which the sorptive agent removes the organic vapor from the dry air.

It has now been found that upon contacting the sorptive agent with a given dry air/organic vapor mixture of constant flow rate that the weight increase of the sorptive agent is directly proportional to the time of exposure, until the time at which the sorptive capacity of the sorptive agent is nearing exhaustion. When the sorptive capacity of the sorptive agent nears exhaustion, the sorptive agent rather promptly loses its property of near total retention of the organic vapor. To assure reproducible results from run to run, the sorptive agent test mixture as well as the given air/organic vapor mixture should be anhydrous.

Weight gain is monitored either continuously or periodically. A satisfactory and economical method is as follows: The sorptive agent is positioned in an enclosed zone, conveniently the enclosed zone can be a cylinder or suitable container. The container holding the sorptive agent is weighed on a balance and its weight recorded. The container and sorptive agent is placed in the system and the sorptive agent subsequently exposed to the flow of dry air/organic vapor mixture for a predetermined interval. The dry air/organic vapor flow is stopped and the container and sorptive agent is reweighed and the gain in weight of the sorptive agent for that particular exposure interval calculated. The above procedure is repeated at least until breakthrough for the particular test sample is reached and detected.

Generally, the predetermined exposure intervals are from 1 to 3 minutes duration, but the intervals selected will vary depending on the properties of the chemical being tested. A weight measuring device is currently commercially available which can be modified, if desired, to continuously monitor the weight gain, thereby avoiding the necessity of stopping the gas flow to make weight determinations. The present invention uses dry air, i.e., air which is substantially free of water vapor so that for the duration of the sorptive agent testing, the weight gain of the sorptive agent will be unaffected by the presence of water vapor. A humidity which is too great results in the sorptive agent gaining weight in a non-linear manner, thereby making determination of the breakthrough time difficult utilizing the invention disclosed herein. Although the present invention uses dry air, the breakthrough times determined by the present invention compare favorably with values determined by conventional methods for systems in which the relative humidity of the air/vapor mixture used is 50%.

Breakthrough time for a particular combination of organic vapor and sorptive agent is determined by plotting the gain in weight of the test samples of sorptive agent versus the duration of exposure to the dry air/organic vapor mix on bilinear type graph paper. Breakthrough time is then identified by noting the point at which the slope of the plotted relationship changes significantly. A simple calculation provides the lifetime of the charged respirator cartridge under investigation.

The invention disclosed herein possesses numerous advantages when compared to conventional methods for predicting the time duration of respirator protection. The present invention uses a static dry air/organic vapor system, i.e., a system wherein a preselected portion of a pre-mixed standard consisting of a known volume of dry air with known quantities of organic vapor contaminants dispersed therein is used. Because the concentrations of the individual components are known, instruments for quantifying vapor components are not required. Instead, all precise measurements are made by weighing using most any suitable weighing means understood in the art. Weighing is easy, precise, inexpensive and of general applicability, therefore the cost of respirator testing is greatly reduced. The fact that weighing is of general applicability is of great significance when compared to conventional methodology because the conventional methodology often needs a different analytical configuration, i.e., different columns, detectors, etc., for each particular organic vapor tested.

Furthermore, the process is believed to be useful for determining respirator protection for most environments in which more than one vapor is present since vapor mixtures are readily prepared and weight gain is still the mode of detection of change. Due to the above mentioned characteristics, the present invention is considerably simpler and faster, and can be used with a smaller quantity of sorptive agent than the conventional method. Another important aspect of the invention is that the tester can rely solely on weight gain since there is a means to detect when channeling occurs and/or if a particular organic vapor passes through the cartridge without being adsorbed. Because the concentration of the various components are known and the flow rate of the dry air/organic vapor mix is also known, the gain in weight of the sorptive agent should take place at a constant rate and can be predicted for any particular time duration of exposure to the dry air/organic vapor mix. Deviations from the expected weight gain indicate that the sorptive agent has failed to completely adsorb the organic vapor being tested.

The invention disclosed herein as indicated above is further directed to a kit which includes apparatus essential for practicing the present invention. A complete kit includes:

Gas tight impermeable plastic or equivalent bags
Set of syringes
Rotameter or similar gas flow measuring device
One or more glass cylinders or similar sorptive agent container
Tubing or similar gas conduit means
Balance or similar weighing device
Recorder
Dry-test meter or similar gas volume measuring device
Vacuum source device
Stop watch or similar timing device
Fittings or similar connection means The present invention also contemplates kits in which at least one or more of the components is omitted since most laboratories will be equipped with at least one of the above mentioned components.

In general, respirator cartridge life is determined as follows: A dry air/organic vapor standard is prepared by methods well understood in the art; however, it is important to use clean dry air which by itself will not increase the weight of the sorptive agent for the duration of the test period. Clean dry air is conveniently obtained by contacting ambient air first with a portion of the same kind of sorptive agent to be tested and subsequently to a desiccant. The clean dry air is then passed through a dry test meter, which measures the volume of the gas and into a receptacle. It is recommended that the receptacle have walls composed of a flexible material which is impermeable to gases and which will not react with or adsorb gases. A collapsible plastic bag with a gas tight closure, gas connection fittings and a volume of 100 liters or greater is recommended since the bag should hold a large enough volume of gas in order that measurable quantities of the contaminants can be added to produce a dry air/organic vapor mixture of known composition. Large volume bags also reduced the number of such mixtures which must be prepared. Known quantities of the volatile contaminants are added to the bag in an appropriate physical state. Bag components are mixed by methods well understood in the art. For example, mixing can be accomplished by physically manipulating the flexible walls of the plastic bag or alternately by fitting the plastic bag with inlet and outlet ports and then circulating the components by means of a pump until the components are mixed.

To carry out the testing of the sorptive agent, the plastic bag containing a known mixture is operatively connected by means of tubing or other gas conduit means to a container, generally a glass cylinder, charged with the sorptive agent to be tested. From the cylinder, the dry air/organic vapor mix is directed to a constant flow rate most easily accomplished by drawing the mixture through a rotameter or similar flow measuring device to a vacuum source such as a vacuum pump, aspirator or building vacuum.

To determine the respirator cartridge life for a particular respirator cartridge, a quantity of the preselected sorptive agent is obtained or the respirator cartridge containing the sorptive agent is disassembled and a representative sample portion of the sorptive agent is removed for use in testing. The particle size rating provided by the manufacturer is noted or alternatively the particle size is determined by known methods. The sorptive agent sample size can be relatively small, for example between 2 and 3 grams, as illustrated in the working example herein. A weighed portion of the sorptive agent is placed into a pre-weighed container, preferably a glass cylinder, which is fitted at both ends with a gas permeable sorptive agent retaining means, such as glass wool. The depth and density of the sorptive agent in the cylinder should approximate the depth and density of the sorptive agent as originally found in the respirator cartridge. A cylinder size is selected which has a ratio of cylinder diameter to the average particle diameter of the sorptive agent equal to or greater than 8:1. This ratio of column diameter to average particle diameter is recommended in order to avoid channeling, i.e., the passage of the dry air/organic vapor mixture through the cylinder charged with sorptive agent without the gas intimately contacting sorptive surfaces. If channeling occurs, the breakthrough time for the test sample will not be an accurate reflection of the ability of the sorptive agent to remove organic vapor contaminants from dry air. The cylinder charged with the sorptive agent is weighed, the preferred method being to dry the filled cylinder over a desiccant to a constant weight.

Once the weight of the cylinder charged with sorptive agent is known, it is placed in the system and the dry air/organic vapor mixture is drawn through the sorptive agent at a flow rate slow enough to avoid channeling or entrainment, generally a linear flow rate of 38 centimeters per second or less. The duration of the exposure of the sorptive agent to the dry air/organic vapor mixture of known preselected composition is timed, generally an interval of from 1 to 3 minutes as previously described, the flow is then stopped, and the weight of the filled cylinder is measured after each predetermined exposure interval.

Because of the substantial volume of dry air/organic vapor mixture of known preselected composition used during a particular test run, it is generally necessary to make up new bags or portion thereof of the same concentration several times during the test. For example, a bag of the same composition can be prepared during the time at which the dry air/organic vapor flow is stopped in order to weigh the filled cylinder, or alternatively a series of bags of identical composition can be prepared prior to testing. During the time required to mix and/or place the new bag of the known mixture in the system, it is recommended that the filled cylinder be put in a sealed container and the container placed in a desiccator.

Respirator cartridge life is calculated as follows: The weight gain of the tested portion of sorptive agent is determined for each interval of exposure to the dry air/organic vapor mixture and the results are tabulated. A plot of the tabulated results is made on bilinear graph paper and represents a plot of weight gain versus time. The plot takes the form of a straight line before the point of breakthrough. However, at the point corresponding to the breakthrough of the contaminant vapor through the tested sorptive agent, the slope of the plot changes.

Breakthrough time for the entire respirator cartridge is calculated by using the following equation:

$$T_{b,r} = T_{b,s} \times \frac{F_s}{F_r} \times \frac{W_r}{W_s}$$

where:

$T_{b,r}$ is the breakthrough time (i.e., useful life) of the respirator cartridge, minutes;

$T_{b,s}$ is the breakthrough time of the cylinder containing the sorptive agent test sample, minutes;

$F_s$ is the flow rate through the cylinder containing the sorptive agent test sample, liters per min.;

$F_r$ is the flow rate through the respirator cartridge, liters per minute;

$W_r$ is the weight of the sorptive agent in the respirator cartridge, grams;

$W_s$ is the weight of the sorptive agent test sample in the filled cylinder, grams.

The value $T_{b,r}$ is the calculated time duration of protection for the particular respirator cartridge being tested. Other units of measurement for time, weight, and flow rates may be used as long as the units are used consistently throughout the calculations.

Results from the use of the present process are compared in Table I with literature values obtained by the much slower and more expensive conventional means.

TABLE I

EXPERIMENTAL RESULTS

| Chemical | Conc. (ppm) | Predicted Breakthrough Time, ($T_{b,r}$), Using the Present Invention (minutes) | Actual 1% Breakthrough Time Using Conventional Methods, as Cited in the Literature (minutes) |
|---|---|---|---|
| Acetone | 1000 | 30 | 37.1 |
| Isopropanol | 1000 | 60 | 54.3 |
| Methyl Chloride | 1000 | <2.7 | 0.05 |
| CCl$_4$ | 1000 | 53 | 77.0 |
| CHCl$_3$ | 1000 | 28 | 33.2 |
| Hexane | 1000 | 42 | 52.3 |
| Toluene | 1000 | 71 | 94.3 |
| Acrylonitrile | 1000 | 51 | 48.5 |
| Ethyl Benzene | 1000 | 67 | 83.7 |
| Vinyl Bromide | 1000 | 29 | 31 |
| Vinyl Bromide | 100 | 91 | 125 |
| Vinyl Bromide | 20 | 198 | 240 |

The data on 1% breakthrough times was obtained from Nelson, G. O. and C. A. Harder: Respirator Cartridge Efficiency Studies: V. Effects of Solvent Vapor, Am. Ind. Hyg. Assoc. J. 33:391 (1974) and the data pertaining to the conventional respirator testing of vinyl bromide was obtained by testing at The Dow Chemical Company. Comparisons between the predicted breakthrough times using the present invention and the 1% breakthrough times cited in the literature were made by making the calculations of the predicted breakthrough times of the present invention utilizing values for $F_r$ and $W_r$ corresponding to the standard conditions for conventional respirator testing.

Table I shows a favorable correlation between the predicted breakthrough times for the present invention and the 1% breakthrough times cited in the literature. The present invention in general uses about 2.1 to about 2.5 grams of carbon and a dry air/organic vapor flow rate of from about 6.0 to about 6.2 liters per minute. Conventional methodology uses a system having 50% relative humidity and a flow rate of 53.3 liters per minute.

The conventional methodology uses a greater volume of gas per unit time since conventional testing exposes the entire respirator cartridge to the contaminant mixture, whereas the present invention uses only a portion of the sorptive agent for test purposes. Even though the Table I data generated by conventional means used a system with 50% relative humidity, the predicted breakthrough times of the two systems correlate nicely. In general, the breakthrough times of the present invention tend to be somewhat shorter than those predicted by conventional means thus providing a built-in safety factor. The shorter breakthrough times of the present invention may be due, at least in part, to the way in which the data is presented and the generally conservative manner in which $T_{b,s}$ has been determined from the plotted data, as illustrated by the determination of $T_{b,s}$ in the working example, infra. Breakthrough times for the present invention correspond to the initial breakthrough, whereas the data for the conventional system reports 1% breakthrough, i.e., the point at which 10 ppm of the organic gas contaminant passes through the cartridge.

The vinyl bromide data of Table I indicates that changes in the concentration of the organic vapor contaminant often are accompanied by changes in $T_{b,r}$ which are not proportional to the change in the concentrations of that organic vapor contaminant; therefore, it is recommended that separate breakthrough time determinations be made when the concentration of a particular organic vapor contaminant varies significantly.

WORKING EXAMPLE

A glass cylinder, 19 mm in diameter, was carefully weighed and packed with 2.29161 grams of desiccated carbon. A Teflon bag was prepared containing 435 microliters toluene dispersed in 100 liters of dry air, giving a toluene concentration of 1000 ppm (vol/vol). The dry air/toluene mixture was drawn through the carbon packed cylinder at 6.2 liters per minute (1pm).

The cylinder containing the sorptive agent test sample was disconnected from the system and weighed after each successive exposure of 2.5 minutes. The weight data obtained is shown in Table II. A plot of the weight gain of the carbon tested versus time of exposure is shown in Graph I. The carbon gained weight at a constant rate for the first 25 minutes of exposure, indicating that all of the toluene was being absorbed. After 25 minutes the rate of weight gain of the carbon steadily dropped, indicating that toluene had broken through the carbon sample.

Breakthrough time for the full respirator cartridge was calculated from the equation:

$$T_{b,r} = T_{b,s} \times \frac{F_s}{F_r} \times \frac{W_r}{W_s}$$

where the variables have the previously defined meanings.

$$T_{b,r} = 25 \times \frac{6.2}{53.3} \times \frac{55.7}{2.29161} =$$

70.7 minutes (rounded off to 71 minutes)

for a 55.7 gram cartridge at 1000 ppm toluene and a flow rate of 53.3 lpm. Nelson, G. O. and C. A. Harder: Respirator Cartridge Efficiency Studies: V. Effects of Solvent Vapor., Am. Ind. Hyg. Assoc. J., 33:391 (1974) report a 1% breakthrough time of 94 minutes for a 55.7 gram cartridge at 1000 ppm toluene and a flow rate of 53.3 lpm.

Table II

TOLUENE DATA 1000 pm Toluene

Weight of the carbon tested: 2.29161 grams
Flow: 6.2 liters/minute of a known preselected mixture consisting of 435 microliters toluene in 100 liters dry air

| Time (min.) | Total Weight of Carbon Tested, Cylinder and Connectors (grams) |
|---|---|
| 0 | 39.18930 |
| 2.5 | 39.23894 |
| 5.5 | 39.29955 |
| 7.5 | 39.33962 |
| 10.0 | 39.39016 |
| 12.5 | 39.44134 |
| 15.0 | 39.49222 |
| Tube placed in desiccator- | New dry air/organic vapor mixture of the same known preselected composition was prepared and inserted into the system. |
| 15.0 | 39.49026 |
| 17.5 | 39.54159 |
| 20.0 | 39.59201 |
| 22.5 | 39.64196 |
| 25.0 | 39.69128 |
| 27.5 | 39.73985 |
| 30.0 | 39.78700 |
| Tube placed in desiccator- | New dry air/organic vapor mixture of the same known preselected composition was prepared and inserted into the system. |
| 30.0 | 39.78505 |
| 32.5 | 39.83145 |
| 35.0 | 39.87238 |
| 37.5 | 39.90632 |
| 40.0 | 39.93283 |
| 42.5 | 39.95367 |
| 45.0 | 39.96986 |
| Tube placed in desiccator- | New dry air/organic vapor mixture of the same known reselected composition was prepared and inserted into the system. |
| 45.0 | 39.96796 |
| 47.5 | 39.98163 |
| 50.0 | 39.98815 |
| 57.5 | 39.99439 |
| 60.0 | 39.99410 |

We claim:

1. A process for predicting the useful life of a respirator cartridge charged with a preselected sorptive agent with respect to a given concentration of a preselected organic vapor in air to be passed through the respirator cartridge at a predetermined linear flow rate and the respirator cartridge being adapted to hold the sorptive agent in a bed of predetermined thickness, which comprises; (a) positioning a portion of the preselected sorptive agent within an enclosed zone in a bed substantially of the same depth as said predetermined thickness within the said cartridge; (b) passing an air/organic vapor mixture through the portion of sorptive agent in said enclosed zone at a constant flow rate, said flow rate being substantially less than that at which either channeling or entrainment occur, said air/organic vapor mixture consisting of dry air admixed with said preselected organic vapor in a preselected concentration; (c) measuring and recording throughout the period of passing the dry air/organic vapor mixture through the enclosed zone, the resulting weight increase of the sorptive agent with respect to the time of exposure to the flow of the preselected dry air/organic vapor mixture at least until the sorptive agent no longer removes the organic vapor from the dry air at a constant rate and breakthrough has occurred; and (d) calculating the useful life of the respirator charged with the preselected sorptive agent according to the formula $$T_{b,r} = T_{b,s} \times \frac{F_s}{F_r} \times \frac{W_r}{W_s}$$

wherein $T_{b,r}$ is the useful life of the respirator cartridge;

$T_{b,s}$ is the breakthrough time of the portion of the preselected sorptive agent in the said enclosed zone;

$F_s$ is the flow rate through the portion of the preselected sorptive agent in said enclosed zone;

$F_r$ is the predetermined flow rate through the respirator cartridge;

$W_r$ is the weight of the preselected sorptive agent in the respirator cartridge; and $W_s$ is the weight of the portion of the preselected sorptive agent in said enclosed zone.

2. The process of claim 1 wherein the constant flow rate of the dry air/organic vapor mixture through the enclosed zone is less than a linear flow rate of 38 centimeters per second.

3. The process of claim 1 wherein the ratio of the diameter of the enclosed zone employed for holding said portion of the preselected sorptive agent to the average particle diameter of said sorptive agent is at least 8:1.

4. The process of claim 1 wherein the breakthrough of the portion of preselected sorptive agent in said enclosed zone is determined by plotting the weight gain of said sorptive agent versus aggregate exposure time of said sorptive agent to the dry air/organic vapor mixture and ascertaining from the plot the point at which the slope of the plot substantially deviates from a straight line, and reading the corresponding time from the time coordinate.

5. A kit for practicing the process of claim 1 comprising a flexible-walled gas impermeable bag with a gas impermeable closure and controlable gas discharge fittings, syringe, gas flow measuring device, container to hold the sorptive agent in a prescribed geometrical configuration, gas conduit means, weighing device, recorder, gas volume measuring device, vacuum source device, timing device, and respective connection means.

* * * * *